US012705760B2

(12) United States Patent
Owaki et al.

(10) Patent No.: US 12,705,760 B2
(45) Date of Patent: Aug. 11, 2026

(54) ANALYSIS DEVICE, ANALYSIS METHOD, ANALYSIS PROGRAM, AND GENERATION DEVICE

(71) Applicant: TOHOKU UNIVERSITY, Sendai (JP)

(72) Inventors: Dai Owaki, Sendai (JP); Yusuke Sekiguchi, Sendai (JP); Keita Honda, Sendai (JP); Shinichi Izumi, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 265 days.

(21) Appl. No.: 18/391,812

(22) Filed: Dec. 21, 2023

(65) Prior Publication Data

US 2024/0169559 A1 May 23, 2024

Related U.S. Application Data

(63) Continuation of application No. PCT/JP2022/005518, filed on Feb. 11, 2022.

(30) Foreign Application Priority Data

Jul. 20, 2021 (JP) ................................ 2021-120060

(51) Int. Cl.

*G06T 7/246* (2017.01)
*A61B 5/00* (2006.01)
*A61B 5/11* (2006.01)

(52) U.S. Cl.

CPC ............ *G06T 7/246* (2017.01); *A61B 5/0077* (2013.01); *A61B 5/112* (2013.01); *A61B 5/1121* (2013.01);

(Continued)

(58) Field of Classification Search

CPC ........... G06T 7/246; G06T 2207/10016; G06T 2207/20081; G06T 2207/30196;

(Continued)

(56) References Cited

U.S. PATENT DOCUMENTS 9,031,691 B2 * 5/2015 Yamane ................. B25J 9/1607 901/1
2016/0345870 A1 12/2016 Ichikawa et al.

FOREIGN PATENT DOCUMENTS

CN 111950383 A 11/2020
WO 2015/129883 A1 9/2015

OTHER PUBLICATIONS

Nathaniel T. Pickle, et al. “Whole-body angular momentum during sloped walking using passive and powered lower-limb prostheses”, Journal of Biomechanics, vol. 49, Issue 14, Oct. 3. 2016 (Year: 2016).*

(Continued)

*Primary Examiner* — Matthew C Bella
(74) *Attorney, Agent, or Firm* — Myers Wolin, LLC

(57) ABSTRACT

An analysis device that analyzes a motion of a target with constitution bodies connected to each other incudes: angular momentum information acquisition processor circuitry configured to acquire angular momentum information representing a time series of angular momentum for each of the constitution bodies; and characteristic information acquisition processor circuitry configured to acquire characteristic information, the characteristic information being based on a first singular vector and representing a characteristic of the motion, the first singular vector corresponding to a first singular value and having elements corresponding to the respective constitution bodies, the first singular value being the largest among singular values of a first matrix whose elements are the angular momentum information for the respective constitution bodies.

14 Claims, 13 Drawing Sheets

(52) U.S. Cl.
CPC .......... *A61B 5/1128* (2013.01); *A61B 5/7267* (2013.01); *A61B 2505/09* (2013.01); *G06T 2207/10016* (2013.01); *G06T 2207/20081* (2013.01); *G06T 2207/30196* (2013.01)

(58) Field of Classification Search
CPC ..... A61B 5/0077; A61B 5/112; A61B 5/1128; A61B 5/7267; A61B 2505/09
See application file for complete search history.

(56) References Cited

OTHER PUBLICATIONS

Nott, C. R., R. R. Neptune, and S. A. Kautz. "Relationships between frontal-plane angular momentum and clinical balance measures during post-stroke hemiparetic walking." Gait & posture 39.1 (2014): 129-134. (Year: 2014).*

Herr, Hugh, and Marko Popovic. "Angular momentum in human walking." Journal of experimental biology 211.4 (2008): 467-481. (Year: 2008).*

Bennett, Bradford C., Thomas Robert, and Shawn D. Russell. "Angular momentum: Insights into walking and its control." 2011 IEEE/RSJ International Conference on Intelligent Robots and Systems. IEEE, 2011. (Year: 2011).*

Popovic, Mako, and Amy Englehart. "Angular momentum primitives for human walking: biomechanics and control." 2004 IEEE/RSJ International Conference on Intelligent Robots and Systems (IROS)(IEEE Cat. No. 04CH37566). vol. 2. IEEE, 2004. (Year: 2004).*

Komura, Taku, et al. "Simulating pathological gait using the enhanced linear inverted pendulum model." IEEE Transactions on biomedical engineering 52.9 (2005): 1502-1513. (Year: 2005).*

Owaki, Dai, et al. "Two-week rehabilitation with auditory biofeedback prosthesis reduces whole body angular momentum range during walking in stroke patients with hemiplegia: A randomized controlled trial." Brain sciences 11.11 (2021): 1461. (Year: 2021).*

Inagaki et al., "Detection of the Body Center of Gravity Using Kinect and its Accurancy", Journal of Clinical Gait Analysis Forum of Japan, 2017, pp. 21-27, vol. 4, No. 1, Japan, with English abstract.

International Search Report issued by the Japan Patent Office for International Patent Application No. PCT/JP2022/005518, mailed on Apr. 19, 2022, with an English translation from WIPO ePCT system.

Mishima et al., "Extraction of Similarities and Differences in Human Behaviors using Singular Value Decomposition", IEICE Journal, 2011, vol. J94-A, No. 4, pp. 293-302, Institute of Electronics, Information and Communication Engineers, Japan, with English abstract.

Okamoto et al., "Attitude Representation for Motion Feature Extraction using Singular Value Decomposition", 2P1-N06, the Japan Society of Mechanical Engineers, No. 12-3 Proceedings of the 2012 JSME Conference on Robotics and Mechatronics, Hamamatsu, Japan, May 2012, with English abstract.

Farrell et al., "Angular Momentum Primitives for Human Turning: Control Implications for Biped Robots", Dec. 2008, pp. 163-167, TP1-7, 8th IEEE-RAS International Conference on Humanoid Robots, Daejeon, Korea.

Orin et al., "Centroidal Momentum Matrix of a Humanoid Robot: Structure and Properties", 2008 IEEE/RSJ International Conference on Intelligent Robots and Systems, IEEE Xplore, Oct. 2008 [https://www.researchgate.net/publication/224339669].

* cited by examiner

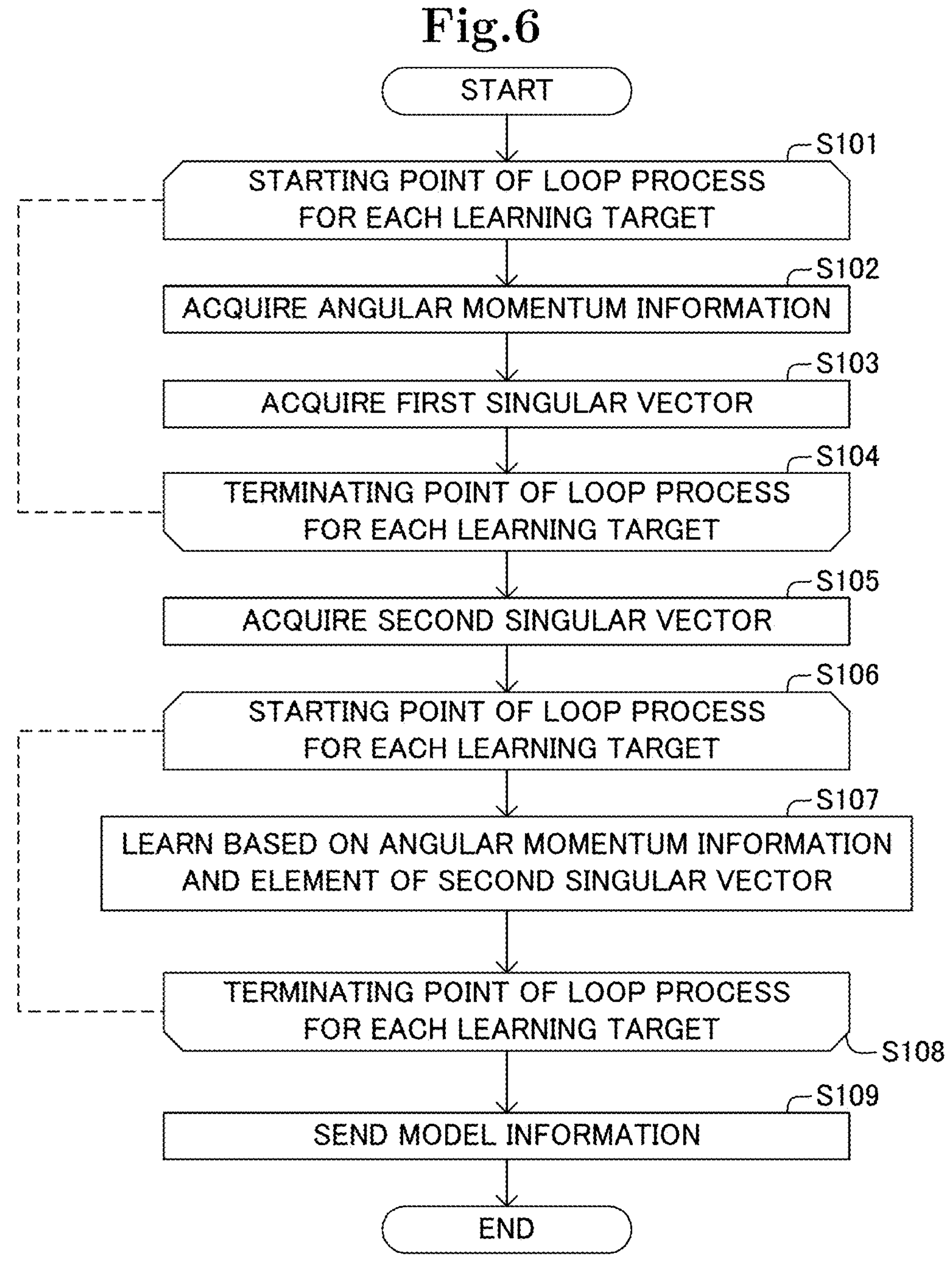
Fig.6
START
S101
STARTING POINT OF LOOP PROCESS FOR EACH LEARNING TARGET
S102
ACQUIRE ANGULAR MOMENTUM INFORMATION
S103
ACQUIRE FIRST SINGULAR VECTOR
S104
TERMINATING POINT OF LOOP PROCESS FOR EACH LEARNING TARGET
S105
ACQUIRE SECOND SINGULAR VECTOR
S106
STARTING POINT OF LOOP PROCESS FOR EACH LEARNING TARGET
S107
LEARN BASED ON ANGULAR MOMENTUM INFORMATION AND ELEMENT OF SECOND SINGULAR VECTOR
TERMINATING POINT OF LOOP PROCESS FOR EACH LEARNING TARGET
S108
S109
SEND MODEL INFORMATION
END

ANALYSIS DEVICE, ANALYSIS METHOD, ANALYSIS PROGRAM, AND GENERATION DEVICE

CROSS-REFERENCE TO RELATED APPLICATION

This application is a continuation application of International Application No. PCT/JP2022/5518, filed on Feb. 11, 2022 and designated the U.S., which claims priority to Japanese Patent Application No. 2021-120060, filed on Jul. 20, 2021, the entire contents of each are incorporated herein by reference.

FIELD

The present disclosure relates to an analysis device, an analysis method, an analysis program, and a generation device.

BACKGROUND

An analysis device that analyzes a motion of a target with constitution bodies connected to each other is known. For example, the analysis device described in Patent Literature 1 analyzes a gait by human. The analysis device acquires an amount of sway in each of a lumbar part and a thoracic dorsal part as characteristic information representing a characteristic in the gait, and displays the acquired characteristic information.

CITATION LIST

Patent Literature
Patent Literature 1: International Publication No. WO2015/129883

SUMMARY

By the way, humans may have paralysis in a half of the body on left side or right side. In this case, the larger disability by the paralysis, the greater difference in the degree to which the constitution bodies contribute to the motion in the gait between the constitution bodies in the left side of the body and the constitution bodies in the right side of the body. For example, the constitution body is a thigh, a lower leg, a foot, an upper arm, a forearm, or the like. Thus, for example, it is easier to evaluate progress in rehabilitation, if the degree to which the constitution bodies contribute to the motion between the constitution bodies in the left side of the body and the constitution bodies in the right side of the body can be known with high accuracy.

However, in the above analysis device, there is a problem that the degree to which the constitution bodies contribute to the motion between the constitution bodies in the left side of the body and the constitution bodies in the right side of the body is not sufficiently reflected in the characteristic information. This kind of problem can occur with motions other than the gait as well.

An object of the present disclosure is to reflect the degree to which each of the constitution bodies contributes to the motion in the characteristic information with high accuracy.

In one aspect, an analysis device analyzes a motion of a target with constitution bodies connected to each other. The analysis device comprises an angular momentum information acquisition unit and a characteristic information acquisition unit. The angular momentum information acquisition unit acquires angular momentum information representing a time series of angular momentum for each of the constitution bodies. The characteristic information acquisition unit acquires characteristic information. The characteristic information is based on a first singular vector and represents a characteristic of the motion. The first singular vector corresponds to a first singular value and has elements corresponding to the respective constitution bodies. The first singular value is the largest among singular values of a first matrix whose elements are the angular momentum information for the respective constitution bodies.

In another aspect, an analysis method analyzes a motion of a target with constitution bodies connected to each other. The analysis method includes acquiring angular momentum information representing a time series of angular momentum for each of the constitution bodies, and acquiring characteristic information. The characteristic information is based on a first singular vector and represents a characteristic of the motion. The first singular vector corresponds to a first singular value and has elements corresponding to the respective constitution bodies. The first singular value is the largest among singular values of a first matrix whose elements are the angular momentum information for the respective constitution bodies.

In another aspect, an analysis program causes a computer to perform a process that analyzes a motion of a target with constitution bodies connected to each other. The process includes acquiring angular momentum information representing a time series of angular momentum for each of the constitution bodies, and acquiring characteristic information. The characteristic information is based on a first singular vector and represents a characteristic of the motion. The first singular vector corresponds to a first singular value and has elements corresponding to the respective constitution bodies. The first singular value is the largest among singular values of a first matrix whose elements are the angular momentum information for the respective constitution bodies.

In another aspect, a generation device generates a trained model used to analyze a motion of a target with constitution bodies connected to each other. The generation device comprises an angular momentum information acquisition unit, a first singular vector acquisition unit, a second singular vector acquisition unit, and a model generation unit.

The angular momentum information acquisition unit acquires angular momentum information for each of learning targets. The angular momentum information represents a time series of angular momentum for each of the constitution bodies.

The first singular vector acquisition unit acquires a first singular vector for each of the learning targets. The first singular vector corresponds to a first singular value and has elements corresponding to the respective constitution bodies. The first singular value is the largest among singular values of a first matrix whose elements are the angular momentum information for the respective constitution bodies.

The second singular vector acquisition unit acquires a second singular vector. The second singular vector corresponds to a second singular value and has elements corresponding to the respective learning targets. The second singular value is the second largest among singular values of a second matrix whose elements are the first singular vectors for the respective learning targets.

The model generation unit generates the trained model by learning teaching data for each of the learning targets. The teaching data includes the angular momentum information of the learning target, and information based on an element of the second singular vector. The element corresponds to the learning target.

The degree to which each of the constitution bodies contributes to the motion can be reflected in the characteristic information with high accuracy.

BRIEF DESCRIPTION OF DRAWING

FIG. 1 is a block diagram illustrating a configuration of an analysis system of a first embodiment.

FIG. 2 is a block diagram illustrating a configuration of a generation device of the first embodiment.

FIG. 6 is a flowchart illustrating a process performed by the generation device of the first embodiment.

DESCRIPTION OF EMBODIMENTS

Figure 3:
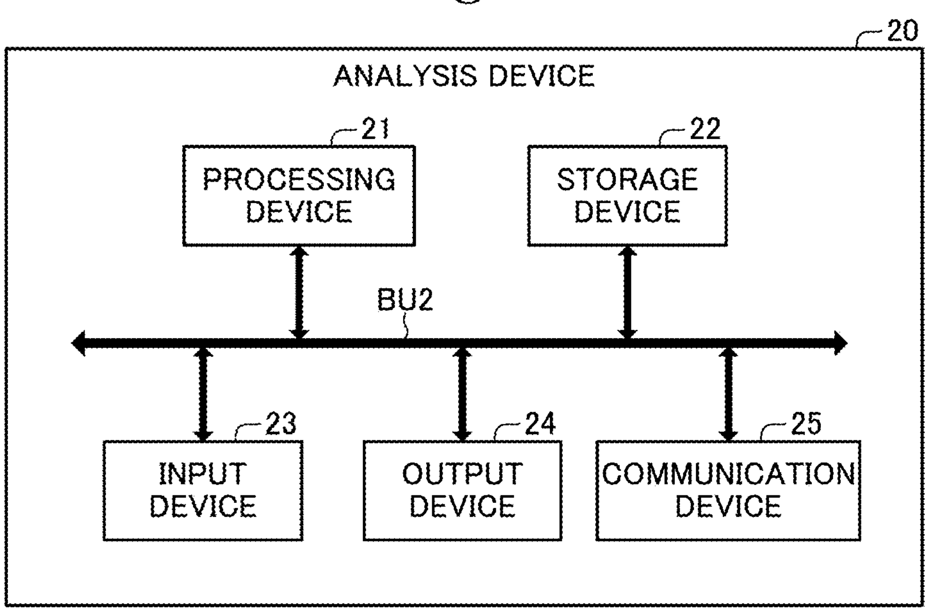
FIG. 3 is a block diagram illustrating a configuration of an analysis device of the first embodiment.

Hereinafter, each embodiment relating to an analysis device, an analysis method, an analysis program, and a generation device of the present disclosure will be described with reference to FIGS. 1 to 11.

First Embodiment

Overview

An analysis device of a first embodiment analyzes a motion of a target with constitution bodies connected to each other. The analysis device comprises an angular momentum information acquisition unit and a characteristic information acquisition unit.

The angular momentum information acquisition unit acquires angular momentum information representing a time series of angular momentum for each of the constitution bodies.

The characteristic information acquisition unit acquires characteristic information. The characteristic information is based on a first singular vector and represents a characteristic of the motion. The first singular vector corresponds to a first singular value and has elements corresponding to the respective constitution bodies. The first singular value is the largest among singular values of a first matrix whose elements are the angular momentum information for the respective constitution bodies.

According to this, the degree to which each of the constitution bodies contributes to the motion is reflected in the first singular vector. Thus, the degree to which each of the constitution bodies contributes to the motion can be reflected in the characteristic information with high accuracy. As a result, the degree to which the constitution bodies contribute to the motion between the constitution bodies in the left side of the body and the constitution bodies in the right side of the body can be known with high accuracy. Therefore, for example, progress in rehabilitation can be properly evaluated.

Next, the analysis system of the first embodiment will be described in detail.

(Configuration)

Figures 1, 2:
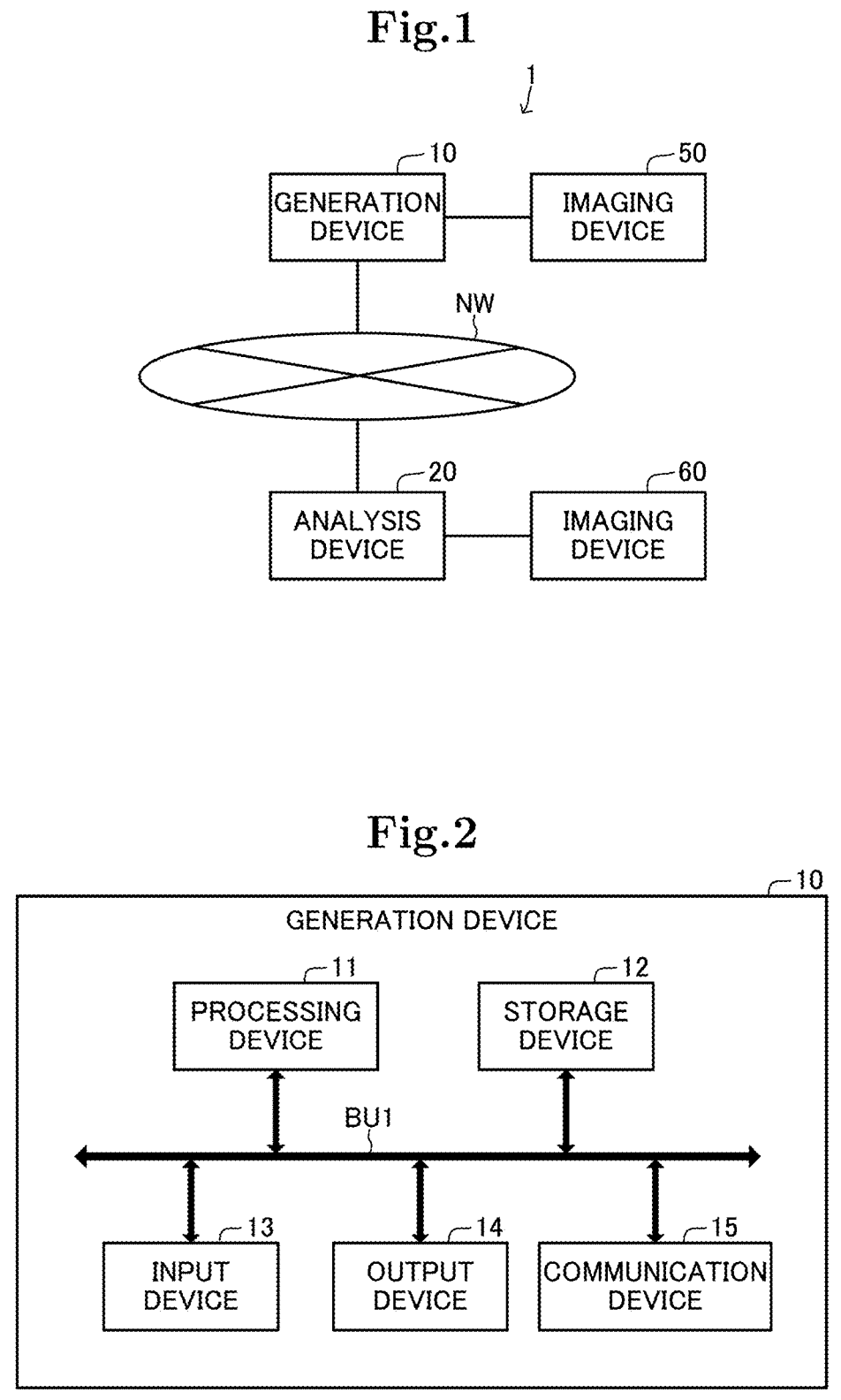

As illustrated in FIG. 1, an analysis system 1 has a generation device 10 and an analysis device 20. The generation device 10 and the analysis device are communicably connected to each other via a communication line NW.

The communication line NW may include a transmission path for wireless communication.

Each of the generation device 10 and the analysis device 20 is an information processing device or a computer. For example, the computer may be at least part of a stationary game machine, a portable game machine, a television receiver, a smartphone, or the like. For example, the generation device 10 may be a server-type computer, a desktop-type computer, a laptop-type computer, a tablet-type computer, a smartphone, or the like. For example, the analysis device 20 may be a desktop-type computer, a laptop-type computer, a tablet-type computer, a smartphone, or the like. Note that each of the generation device 10 and the analysis device 20 may be composed of multiple devices that are communicably connected to each other.

As illustrated in FIG. 2, the generation device 10 includes a processing device 11, a storage device 12, an input device 13, an output device 14, and a communication device 15, which are connected to each other via a bus Bill.

The processing device 11 controls the storage device 12, the input device 13, the output device 14, and the communication device 15 by executing a program stored in the storage device 12. As a result, the processing device 11 realizes a function described later.

In this example, the processing device 11 is a Central Processing Unit (CPU). Note that the processing device 11 may include a Micro Processing Unit (MPU), a Graphics Processing Unit (GPU), or a Digital Signal Processor (DSP) instead of or in addition to the CPU.

In this example, the storage device 12 includes a volatile memory and a non-volatile memory. For example, the storage device 12 includes at least one of a Random Access Memory (RAM), a Read Only Memory (ROM), a semiconductor memory, an organic memory, a Hard Disk Drive (HDD), and a Solid State Drive (SSD).

The input device 13 accepts information input from the outside of the generation device 10. In this example, the input device 13 includes a keyboard and a mouse. Note that the input device 13 may include a microphone. The input device 13 is connected to an imaging device 50.

The imaging device 50 includes a first imaging unit and a second imaging unit. The first imaging unit photographs a target and acquires a visible light image representing the photographed target. The visible light image is an image representing the intensity of visible light reflected by the target for each of multiple pixels. In this example, the pixels included in the visible light image have a grid-like arrangement.

In this example, the first imaging unit includes a color camera or a Red Green Blue (RGB) camera. Note that the first imaging unit may be a black and white camera. In this example, the first imaging unit acquires visible light video information representing a time series of the visible light image.

The second imaging unit photographs the target and acquires a distance image representing the photographed target. The distance image is an image representing the distance between a reference plane and the target for each of multiple pixels. In this example, the reference plane forms a vertical plane. Note that the reference plane may be inclined to the vertical plane. In this example, the pixels included in the distance image have a grid-like arrangement.

In this example, the second imaging unit includes a Time Of Flight (TOF) camera. Note that the second imaging unit may acquire the distance image by using a stereo camera instead of the TOF camera. The second imaging unit may also acquire the distance image by using a distance measuring sensor measuring the distance between the reference plane and the target for each of multiple pixels with the grid-like arrangement. In this example, the second imaging unit acquires distance video information representing a time series of the distance image.

For the input device 13, the visible light video information and the distance video information acquired by the imaging device 50 are input.

Note that the imaging device 50 may constitute a part of the generation device 10.

The output device 14 outputs information to the outside of the generation device 10. In this example, the output device 14 includes a display. Note that the output device 14 may include a speaker.

Note that the generation device 10 may include a touch panel display, which constitutes both the input device 13 and the output device 14.

The communication device 15 communicates with a device outside the generation device 10. In this example, the communication device 15 includes a card-type or on-board-type network adapter or a network interface.

As illustrated in FIG. 3, the analysis device 20 includes a processing device 21, a storage device 22, an input device 23, an output device 24, and a communication device 25, which are connected to each other via a bus BU2. The processing device 21, the storage device 22, the input device 23, the output device 24, and the communication device 25 have functions similar to the processing device 11, the storage device 12, the input device 13, the output device 14, and the communication device 15 of the generation device 10, respectively.

The input device 23 is connected to an imaging device 60. The imaging device 60 is configured similarly to the imaging device 50. For the input device 23, the visible light video information and the distance video information acquired by the imaging device 60 are input.

Note that the imaging device 60 may constitute a part of the analysis device 20.

(Function)

The generation device 10 generates a trained model. The trained model is used to analyze a motion of a target with constitution bodies connected to each other.

In this example, the target is a human with paralysis in a half of the body on left side or right side. The target may be a human without paralysis. The target may also be an animal other than the human (e.g., a dog, cat, or horse).

In this example, the constitution bodies are eleven constitution bodies consisting of a forearm, an upper arm, a thigh, a lower leg, and a foot, each included in a half of the body with paralysis, a forearm, an upper arm, a thigh, a lower leg, and a foot, each included in another half of the body without paralysis, and a pelvic region. Note that the constitution bodies may be a part of the above eleven constitution bodies. Alternatively, the constitution bodies may include another constitution body in addition to the above eleven constitution bodies.

In this example, the motion is a gait. Note that the motion may be a motion other than the gait (for example, a motion for getting up, a motion for sitting, a motion for standing, running, pitching, swimming, etc.).

Figure 4:
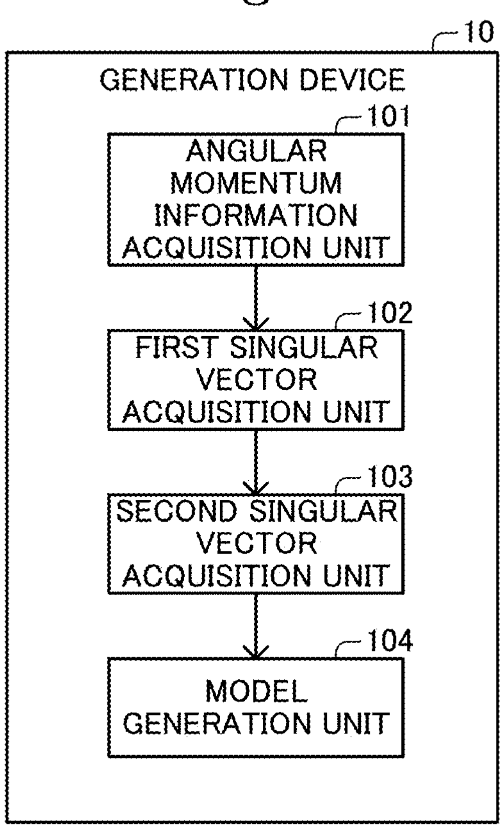
FIG. 4 is a block diagram illustrating a function of the generation device of the first embodiment.

As illustrated in FIG. 4, a function of the generation device 10 includes an angular momentum information acquisition unit 101, a first singular vector acquisition unit 102, a second singular vector acquisition unit 103, and a model generation unit 104.

The angular momentum information acquisition unit 101 acquires angular momentum information based on the visible light video information and the distance video information acquired by the imaging device 50 for each of multiple (in this example, K) learning targets. K represents an integer of 2 or more.

The angular momentum information represents a time series of angular momentum of each of the constitution bodies during a certain motion period. For example, the motion period corresponds to one period when the motion is periodic. In this example, the motion period corresponds to a period with two steps composed of one step on each side. In this example, the motion period begins at a time point when the foot included in the half of the body with paralysis is grounded and ends at a time point when the foot is grounded again after the foot leaves the ground.

In this example, the angular momentum information is acquired as follows.

The angular momentum information acquisition unit 101 estimates multiple (in this example, 14) time series of skeleton constitution positions in the motion period based on the visible light video information and the distance video information.

Each of the multiple skeleton constitution positions corresponds to any one of both ends of the eleven constitution bodies. In this example, the 14 skeleton constitution positions include a wrist part, an elbow part, a shoulder part, a buttock part, a knee part, an ankle part, and a toe part, each included in the right side of the body, and a wrist part, an elbow part, a shoulder part, a buttock part, a knee part, an ankle part, and a toe part, each included in the left side of the body.

The buttock part included in the right side of the body and the buttock part included in the left side of the body constitute the both ends of the pelvic region. The wrist part and the elbow part constitute the both ends of the forearm. The elbow part and the shoulder part constitute the both ends of the upper arm. The buttock part and the knee part constitute the both ends of the thigh. The knee part and the ankle part constitute the both ends of the lower leg. The ankle part and the toe part constitute the both ends of the foot.

The angular momentum information acquisition unit 101 estimates, in the motion period, a time series of the position $R^{(k)}_w(t_j)$ of the center of gravity of the entire of the target, a time series of the velocity $V^{(k)}_w(t_j)$ of the center of gravity of the entire of the target, a time series of the position $R^{(k)}_i(t_j)$ of the center of gravity of each of the constitution bodies, a time series of the velocity $V^{(k)}_i(t_j)$ of the center of gravity of each of the constitution bodies, and a time series of the angular velocity $\Omega^{(k)}_i(t_j)$ of each of the constitution bodies based on the estimated time series of the skeleton constitution positions.

For example, the above estimation may be made using the techniques according to Non-Patent Literature 1 below.

(Non-patent Literature 1) Jun Inagaki, and 4 others, "Detection of the Body Center of Gravity Using Kinect and its Accuracy," Journal of Clinical Gait Analysis Forum of Japan, The Clinical Gait Analysis Forum of Japan, 2017, Volume 4, Issue 1, p. 21-27 k represents an integer between 1 and K. In this example, the superscript "(k)" for a variable represents a value for the k-th learning target.

i represents an integer between 1 and I. I represents an integer of 2 or more. In this example, I represents 11. In this example, the subscript "i" for a variable represents a value for the i-th constitution body. In this example, the first constitution body corresponds to the pelvic region. The second through sixth constitution bodies correspond to the upper arm, the forearm, the thigh, the lower leg, and the foot, respectively, which are included in the half of the body without paralysis. The seventh through eleventh constitution bodies corresponds to the foot, the lower leg, the thigh, the forearm, and the upper arm, respectively, which are included in the half of the body with paralysis.

$t_j$ represents time. j represents an integer between 1 and J. J represents an integer of 2 or more. In this example, J represents 100. In this example, $t_1$ through $t_J$ correspond to J time points that divide the motion period equally.

The angular momentum information acquisition unit 101 estimates a time series of the angular momentum $L^{(k)}_i(t_j)$ of each of the constitution bodies in the motion period based on the above estimated time series group, and the below Formulae 1 and 2. Thereby, the angular momentum information acquisition unit 101 acquires the angular momentum information representing a time series of the angular momentum $L^{(k)}_i(t_j)$ of each of the constitution bodies.

$$L_i^{(k)}(t_j) = B_i^{(k)}(t_j) \cdot D^{(k)} \qquad \text{[Formula 1]}$$

$$B_i^{(k)}(t_j) = \left(R_i^{(k)}(t_j) - R_w^{(k)}(t_j)\right) \times m_i^{(k)}\left(V_i^{(k)}(t_j) - V_w^{(k)}(t_j)\right) + M_i^{(k)}\Omega_i^{(k)}(t_j) \qquad \text{[Formula 2]}$$

$B^{(k)}_i(t_j)$ represents an angular momentum vector of the i-th constitution body. $D^{(k)}$ represents a reference vector that is a unit vector representing a direction of rotation as a reference. In this example, the reference vector $D^{(k)}$ represents the unit vector that is orthogonal to the frontal plane (in other words, the coronal plane), and is directed toward the rear (from ventral to dorsal) of the target when the half of the body on right side has the paralysis, while is directed toward the front (from dorsal to ventral) of the target when the half of the body on left side has the paralysis.

Therefore, in this example, the angular momentum $L^{(k)}_i(t_j)$ represents a component of the angular momentum vector $B^{(k)}_i(t_j)$ around the rotation axis orthogonal to the frontal plane.

$m^{(k)}_i$ represents the mass of the i-th constitution body. $M^{(k)}_i$ represents the moment of inertia of the i-th constitution body. For example, the mass $m^{(k)}_i$ and the moment of inertia $M^{(k)}_i$ are predetermined values. Note that at least one of the mass $m^{(k)}_i$ and the moment of inertia $M^{(k)}_i$ may be a value input by a user of the generation device 10, or a value estimated based on the visible light video information and the distance video information.

In this example, the angular momentum information is acquired in this way.

The first singular vector acquisition unit 102 generates a first matrix $A^{(k)}_i$ based on the angular momentum information acquired by the angular momentum information acquisition unit 101. As represented in the below Formula 3, the first matrix $A^{(k)}_i$ has elements which are the angular momentum information for the respective constitution bodies.

$$A_1^{(k)} = \begin{bmatrix} L_1^{(k)}(t_1) & L_2^{(k)}(t_1) & \dots & L_I^{(k)}(t_1) \\ L_1^{(k)}(t_2) & L_2^{(k)}(t_2) & \dots & L_I^{(k)}(t_2) \\ \vdots & \vdots & \ddots & \vdots \\ L_1^{(k)}(t_J) & L_2^{(k)}(t_J) & \dots & L_I^{(k)}(t_J) \end{bmatrix} \qquad \text{[Formula 3]}$$

As represented in the below Formulae 4 through 7, the first singular vector acquisition unit 102 acquires a first singular vector $z^{(k)}_i$ by performing singular value decomposition of the generated first matrix $A^{(k)}_i$. The first singular vector $z^{(k)}_i$ is a singular vector (in this example, a right-singular vector) which corresponds to a first singular value $\lambda^{(k)}_i$, and has elements corresponding to the respective constitution bodies. The first singular value $\lambda^{(k)}_i$ is the largest among singular values of the first matrix $A^{(k)}_i$.

In this example, the superscript "T" for a variable represents a transposed matrix.

$$A_1^{(k)} = U^{(k)}\Lambda^{(k)}Z^{(k)T} \qquad \text{[Formula 4]}$$

$$U^{(k)} = \left[ u_1^{(k)} \; u_2^{(k)} \; \dots \; u_J^{(k)} \right] = \begin{bmatrix} u_{1,1}^{(k)} & u_{1,2}^{(k)} & \dots & u_{1,J}^{(k)} \\ u_{2,1}^{(k)} & u_{2,2}^{(k)} & \dots & u_{2,J}^{(k)} \\ \vdots & \vdots & \ddots & \vdots \\ u_{J,1}^{(k)} & u_{J,2}^{(k)} & \dots & u_{J,J}^{(k)} \end{bmatrix} \qquad \text{[Formula 5]}$$

$$\Lambda^{(k)} = \begin{bmatrix} \lambda_1^{(k)} & 0 & 0 & 0 \\ 0 & \lambda_2^{(k)} & \dots & 0 \\ \vdots & \vdots & \ddots & \vdots \\ 0 & 0 & \dots & \lambda_I^{(k)} \\ & 0 & & \end{bmatrix} \text{ where } \qquad \text{[Formula 6]}$$

$$\lambda_i^{(k)} \geq \lambda_{i+1}^{(k)} > 0 (1 \leq i \leq I-1)$$

$$Z^{(k)} = \left[ z_1^{(k)} \; z_2^{(k)} \; \dots \; z_I^{(k)} \right] = \begin{bmatrix} z_{1,1}^{(k)} & z_{1,2}^{(k)} & \dots & z_{1,I}^{(k)} \\ z_{2,1}^{(k)} & z_{2,2}^{(k)} & \dots & z_{2,I}^{(k)} \\ \vdots & \vdots & \ddots & \vdots \\ z_{I,1}^{(k)} & z_{I,2}^{(k)} & \dots & z_{I,I}^{(k)} \end{bmatrix} \qquad \text{[Formula 7]}$$

The first singular vector acquisition unit 102 acquires the first singular vector $z^{(k)}_i$ for each of the learning targets.

The second singular vector acquisition unit 103 generates a second matrix $A_2$ represented by the below Formula 8 based on the first singular vector $z^{(k)}_i$ acquired by the first singular vector acquisition unit 102. As represented in the Formula 8, the second matrix $A_2$ has elements which are the first singular vectors $z^{(k)}_i$ for the respective learning targets.

$$A_2 = \begin{bmatrix} z_{1,1}^{(1)} & z_{2,1}^{(1)} & \dots & z_{I,1}^{(1)} \\ z_{1,1}^{(2)} & z_{2,1}^{(2)} & \dots & z_{I,1}^{(2)} \\ \vdots & \vdots & \ddots & \vdots \\ z_{1,1}^{(K)} & z_{2,1}^{(K)} & \dots & z_{I,1}^{(K)} \end{bmatrix} \qquad \text{[Formula 8]}$$

As represented in the below Formulae 9 through 12, the second singular vector acquisition unit 103 acquires a second singular vector $p_2$ by performing singular value decomposition of the generated second matrix $A_2$. The second singular vector $p_2$ is a singular vector (in this example, a left-singular vector) which corresponds to a second singular value $\gamma_2$, and has elements corresponding to the respective learning targets. The second singular value $\gamma_2$ is the second largest among singular values of the second matrix $A_2$.

$$A_2 = P\Gamma Y^T \quad \text{[Formula 9]}$$

$$P = [\,p_1 \;\; p_2 \;\; \ldots \;\; p_K\,] = \begin{bmatrix} p_{1,1} & p_{1,2} & \cdots & p_{1,K} \\ p_{2,1} & p_{2,2} & \cdots & p_{2,K} \\ \vdots & \vdots & \ddots & \vdots \\ p_{K,1} & p_{K,2} & \cdots & p_{K,K} \end{bmatrix} \quad \text{[Formula 10]}$$

$$\Gamma = \begin{bmatrix} \gamma_1 & 0 & & 0 & 0 \\ 0 & \gamma_2 & & \ldots & 0 \\ \vdots & \vdots & & \ddots & \vdots \\ 0 & 0 & & \ldots & \gamma_I \\ & & 0 & & \end{bmatrix} \text{ where } \gamma_i \geq \gamma_{i+1} > 0 (1 \leq i \leq I-1) \quad \text{[Formula 11]}$$

$$Y = [\,y_1 \;\; y_2 \;\; \ldots \;\; y_I\,] = \begin{bmatrix} y_{1,1} & y_{1,2} & \cdots & y_{1,I} \\ y_{2,1} & y_{2,2} & \cdots & y_{2,I} \\ \vdots & \vdots & \ddots & \vdots \\ y_{I,1} & y_{I,2} & \cdots & y_{I,I} \end{bmatrix} \quad \text{[Formula 12]}$$

In this example, the k-th element $p_{k,2}$ of the second singular vector $p_2$ represents a characteristic which is unique to the motion of the k-th learning target relative to the average motion of a learning target group consisting of the K learning targets. In this example, the magnitude of the k-th element $p_{k,2}$ of the second singular vector $p_2$ is larger as the difference between the average motion of the learning target group and the motion of the k-th learning target is larger.

The model generation unit 104 generates a trained model based on the second singular vector $p_2$ acquired by the second singular vector acquisition unit 103.

In this example, the trained model is generated by learning teaching data for each of the learning targets. The teaching data includes the angular momentum information $L^{(k)}_i(t_j)$ of the learning target, and the element $p_{k,2}$ corresponding to the learning target of the second singular vector $p_2$.

Note that the trained model may be generated by learning teaching data for each of the learning targets. The teaching data includes the angular momentum information $L^{(k)}_i(t_j)$ of the learning target, and a value obtained by multiplying the second singular value $\gamma_2$ to the element $p_{k,2}$ corresponding to the learning target of the second singular vector $p_2$.

Alternatively, the trained model may be generated by learning teaching data for each of the learning targets. The teaching data includes the angular momentum information $L^{(k)}_i(t_j)$ of the learning target, and sign information of the element $p_{k,2}$ corresponding to the learning target of the second singular vector $p_2$. For example, the sign information represents "+1" when the element $p_{k,2}$ is positive, and represents "−1" when the element $p_{k,2}$ is negative.

Alternatively, the trained model may be generated by learning teaching data for each of the learning targets. The teaching data includes the angular momentum information $L^{(k)}_i(t_j)$ of the learning target, and segment information of the element $p_{k,2}$ corresponding to the learning target of the second singular vector $p_2$. For example, the segment information represents a segment (in other words, a class) that contains a value of the element $p_{k,2}$ among predetermined multiple segments. Note that the segment information may represent a segment that contains the magnitude of the value of the element $p_{k,2}$ among predetermined multiple segments.

Alternatively, the angular momentum information $L^{(k)}_i(t_j)$ included in the teaching data may only correspond to a part of the motion period. For example, the trained model may be generated by performing cross-validation.

The trained model includes a neural network. In this example, the trained model includes a recurrent (in other words, recursive) neural network (RNN; Recurrent Neural Network). In this example, the trained model includes LSTM (Long Short Term Memory). In this example, the LSTM is Deep Bidirectional LSTM (DBLSTM). Note that the trained model may include an RNN other than LSTM.

The model generation unit 104 sends model information to the analysis device 20. The model information represents the generated trained model.

The analysis device 20 analyzes a motion of a target of interest based on the trained model generated by the generation device 10, and the visible light video information and the distance video information acquired for the target of interest.

Figure 5:
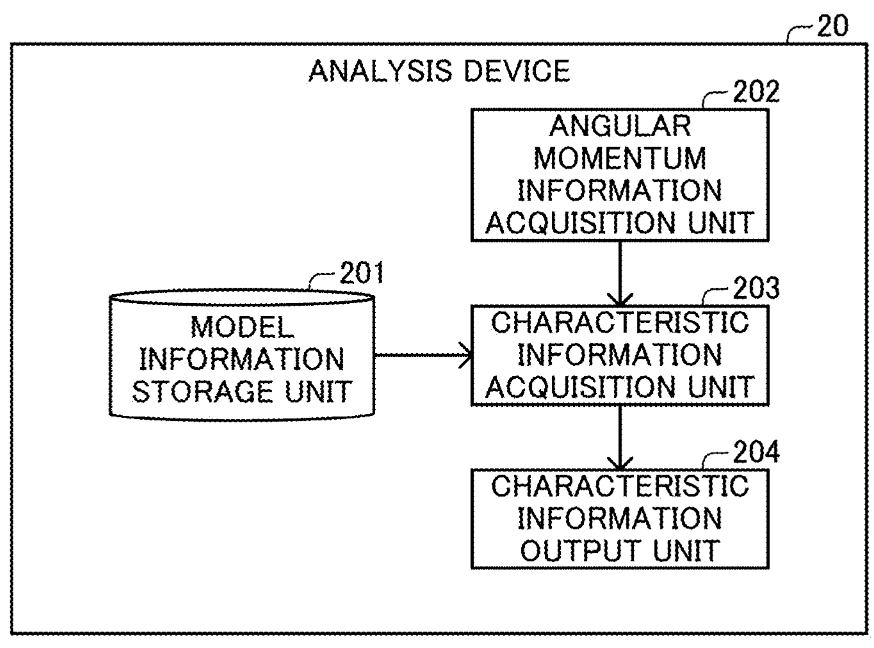
FIG. 5 is a block diagram illustrating a function of the analysis device of the first embodiment.

As illustrated in FIG. 5, a function of the analysis device 20 includes a model information storage unit 201, an angular momentum information acquisition unit 202, a characteristic information acquisition unit 203, and a characteristic information output unit 204.

The model information storage unit 201 receives the model information generated by the generation device 10 from the generation device 10, and stores the received model information in the storage device 22.

The angular momentum information acquisition unit 202 acquires, for the target of interest, angular momentum information based on the visible light video information and the distance video information acquired by the imaging device 60. The angular momentum information acquisition unit 202 acquires the angular momentum information using a similar method to the angular momentum information acquisition unit 101.

The characteristic information acquisition unit 203 acquires characteristic information for the target of interest based on the trained model represented by the model information stored in the model information storage unit 201, and the angular momentum information for the target of interest acquired by the angular momentum information acquisition unit 202. The characteristic information represents a characteristic of the motion of the target of interest.

In this example, the characteristic information represents a value estimated as an element corresponding to the target of interest among the learning targets of the second singular vector $p_2$ acquired for the learning targets when the target of interest is assumed to be included in the learning targets based on which the trained model is generated. Thus, in this example, the characteristic information corresponds to information based on the element which corresponds to the target of interest among the multiple targets of the second singular vector $p_2$. The characteristic information is also information which is generated based on the first singular vector $z^{(k)}_i$. Thus, in this example, the characteristic information corresponds to information based on the first singular vector $z^{(k)}_i$.

The characteristic information output unit 204 outputs the characteristic information acquired by the characteristic information acquisition unit 203 via the output device 24 (in this example, displays it on a display).

In addition to or instead of the characteristic information, the characteristic information output unit 204 may output output information associated with the characteristic information. For example, the output information may represent progress in rehabilitation, or normality of the motion. In this case, the output information may represent that the smaller value represented by the characteristic information, the higher progress in rehabilitation, or the higher normality of the motion.

Note that the analysis device 20 may also have the function of the generation device 10 in addition to the function of the analysis device 20. In this case, the analysis system 1 may lack the generation device 10 and the imaging device 50.

(Operation)

Next, an operation of the analysis system 1 is described with reference to FIGS. 6 and 7.

In this example, the generation device 10 executes a process illustrated in FIG. 6 to generate the trained model.

Specifically, the generation device 10 executes a first loop process (Steps S101 to S104) in which each of the K learning targets is sequentially used as a processing target.

In the first loop process, the generation device 10 acquires, for the learning target as the processing target, the angular momentum information based on the visible light video information and the distance video information acquired by the imaging device 50 (Step S102). Next, the generation device 10 acquires the first singular vector $z^{(k)}_i$ based on the acquired angular momentum information (Step S103).

After executing the first loop process for all of the learning targets, the generation device 10 acquires the second singular vector $p_2$ based on the first singular vector $z^{(k)}_i$ acquired for each of the K learning targets (Step S105).

Next, the generation device 10 executes a second loop process (Steps S106 to S108) in which each of the K learning targets is sequentially used as a processing target.

In the second loop process, the generation device 10 learns, for the learning target as the processing target, the teaching data which includes the angular momentum information $L^{(k)}_i(t_j)$ acquired at Step S102, and the element $p_{k,2}$ corresponding to the learning target of the second singular vector $p_2$ acquired at Step S105 (Step S107).

After executing the second loop process for all of the learning targets, the generation device 10 sends the model information representing the generated trained model to the analysis device 20 (Step S109).

In this way, the generation device 10 executes the process illustrated in FIG. 6.

The analysis device 20 also receives the model information from the generation device 10, and stores the received model information in the storage device 22 by executing a process not illustrated in the drawings.

Figure 7:
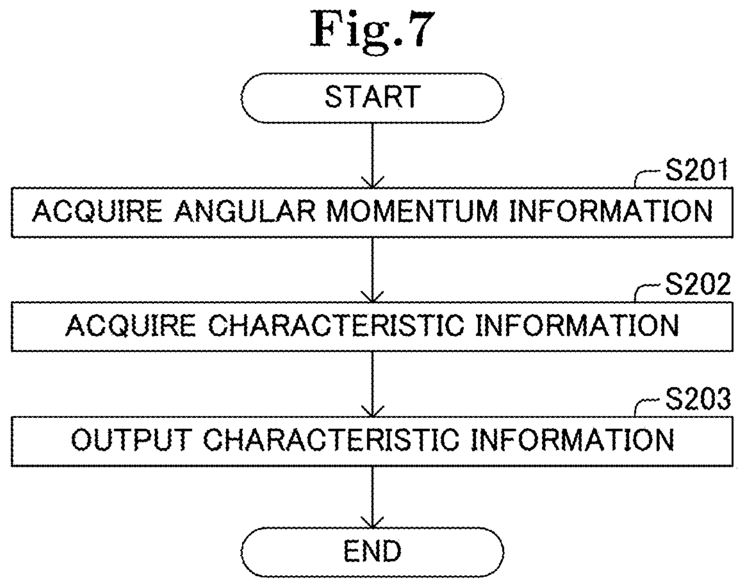
FIG. 7 is a flowchart illustrating a process performed by the analysis device of the first embodiment.

In this example, the analysis device 20 executes a process illustrated in FIG. 7 to analyze the motion of the target of interest based on the trained model generated by the generation device 10, and the visible light video information and the distance video information acquired for the target of interest.

Specifically, the analysis device 20 acquires, for the target of interest, the angular momentum information based on the visible light video information and the distance video information acquired by the imaging device 60 (Step S201). Next, the analysis device 20 acquires the characteristic information for the target of interest based on the trained model represented by the model information stored in the storage device 22, and the angular momentum information acquired at Step S201 (Step S202).

Next, the analysis device 20 outputs the characteristic information acquired at Step S202 via the output device 24 (Step S203).

In this way, the analysis device 20 executes the process illustrated in FIG. 7.

As described above, an analysis device 20 of the first embodiment analyzes a motion of a target with constitution bodies connected to each other.

The analysis device 20 includes an angular momentum information acquisition unit 202 and a characteristic information acquisition unit 203. The angular momentum information acquisition unit 202 acquires angular momentum information representing a time series of angular momentum for each of the constitution bodies. The characteristic information acquisition unit 203 acquires characteristic information. The characteristic information is based on a first singular vector and represents a characteristic of the motion of the target. The first singular vector corresponds to a first singular value and has elements corresponding to the respective constitution bodies. The first singular value is the largest among singular values of a first matrix whose elements are the angular momentum information for the respective constitution bodies.

According to this, the degree to which each of the constitution bodies contributes to the motion is reflected in the first singular vector. Thus, the degree to which each of the constitution bodies contributes to the motion can be reflected in the characteristic information with high accuracy. As a result, the degree to which the constitution bodies contribute to the motion between the constitution bodies in the left side of the body and the constitution bodies in the right side of the body can be known with high accuracy. Therefore, for example, progress in rehabilitation can be properly evaluated.

Furthermore, in the analysis device 20 of the first embodiment, the characteristic information is based on an element of a second singular vector. The element corresponds to a target of interest among targets. The second singular vector corresponds to a second singular value and has elements corresponding to the respective targets. The second singular value is the second largest among singular values of a second matrix whose elements are the first singular vectors for the respective targets.

According to this, in the target group consisting of the targets, the characteristic which is unique to the motion of each of the targets is reflected in the second singular vector. Thus, in the target group, the characteristic which is unique to the motion of the target of interest can be reflected in the characteristic information with high accuracy. As a result, for example, the characteristic which is unique to the motion of the target of interest relative to the average motion of the target group can be known with high accuracy.

Further, in the analysis device 20 of the first embodiment, the characteristic information acquisition unit 203 acquires the characteristic information based on a trained model and the angular momentum information for the target of interest. The trained model is generated by acquiring a second singular vector, and learning teaching data for each of learning targets. The second singular vector corresponds to a second singular value and has elements corresponding to the respective learning targets. The second singular value is the second largest among singular values of a second matrix whose elements are the first singular vectors for the respective learning targets. The teaching data includes the angular momentum information of the learning target, and information based on an element of the second singular vector. The element corresponds to the learning target.

According to this, in the target group consisting of the targets, the characteristic which is unique to the motion of each of the targets is reflected in the second singular vector. Thus, in the target group, the characteristic which is unique to the motion of the target of interest can be reflected in the characteristic information with high accuracy. As a result, for example, the characteristic which is unique to the motion of the target of interest relative to the average motion of the target group can be known with high accuracy. Also, the characteristic information for the target of interest can be acquired more quickly than when calculating the second singular vector for the target group that includes the target of interest.

Furthermore, in the analysis device 20 of the first embodiment, the target is a human with paralysis in a half of the body on left side or right side. The constitution bodies includes a forearm, an upper arm, a thigh, a lower leg and a foot, each included in the half of the body with paralysis, a forearm, an upper arm, a thigh, a lower leg and a foot, each included in another half of the body without paralysis, and a pelvic region.

According to this, the elements of the first matrix correspond to the constitution bodies included in the half of the body with paralysis, and the constitution bodies included in the half of the body without paralysis. As a result, the degree to which the constitution bodies contribute to the motion between the constitution bodies included in the half of the body with paralysis and the constitution bodies included in the half of the body without paralysis can be known with high accuracy. Therefore, for example, progress in rehabilitation can be properly evaluated.

Furthermore, in the analysis device 20 of the first embodiment, the motion is a gait. The angular momentum information corresponds to a period with two steps composed of one step on each side.

In the gait by a healthy person, the degree to which the constitution bodies contribute to the motion is expected to be the same between the constitution bodies included in the half of the body on left side and the constitution bodies included in the half of the body on right side. Thus, according to the analysis device 20, the degree to which the gait is appropriate can be evaluated with high accuracy. Therefore, for example, progress in rehabilitation can be properly evaluated.

A generation device 10 of the first embodiment generates a trained model used to analyze a motion of a target with constitution bodies connected to each other.

The generation device 10 includes an angular momentum information acquisition unit 101, a first singular vector acquisition unit 102, a second singular vector acquisition unit 103, and a model generation unit 104.

The angular momentum information acquisition unit 101 acquires angular momentum information for each of learning targets. The angular momentum information represents a time series of angular momentum for each of the constitution bodies.

The first singular vector acquisition unit 102 acquires a first singular vector for each of the learning targets. The first singular vector corresponds to a first singular value and has elements corresponding to the respective constitution bodies. The first singular value is the largest among singular values of a first matrix whose elements are the angular momentum information for the respective constitution bodies.

The second singular vector acquisition unit 103 acquires a second singular vector. The second singular vector corresponds to a second singular value and has elements corresponding to the respective learning targets. The second singular value is the second largest among singular values of a second matrix whose elements are the first singular vectors for the respective learning targets.

The model generation unit 104 generates the trained model by learning teaching data for each of the learning targets. The teaching data includes the angular momentum information of the learning target, and information based on an element of the second singular vector. The element corresponds to the learning target.

According to this, in the learning target group consisting of the learning targets, the characteristic which is unique to the motion of each of the learning targets is reflected in the second singular vector. Thus, the characteristic which is unique to the motion of each of the learning targets relative to the average motion of the learning target group can be reflected in the trained model with high accuracy. As a result, by acquiring the characteristic information based on the trained model, the characteristic which is unique to the motion of the target of interest can be reflected in the characteristic information with high accuracy. Also, the characteristic information for the target of interest can be acquired more quickly than when calculating the second singular vector for the learning target group that includes the target of interest.

FIGS. 8A, 8B, 9A and 9B are graphs illustrating an example of the results of singular value decomposition of the first matrix $A_1$ calculated by the analysis system 1 of the first embodiment.

Figure 8A:
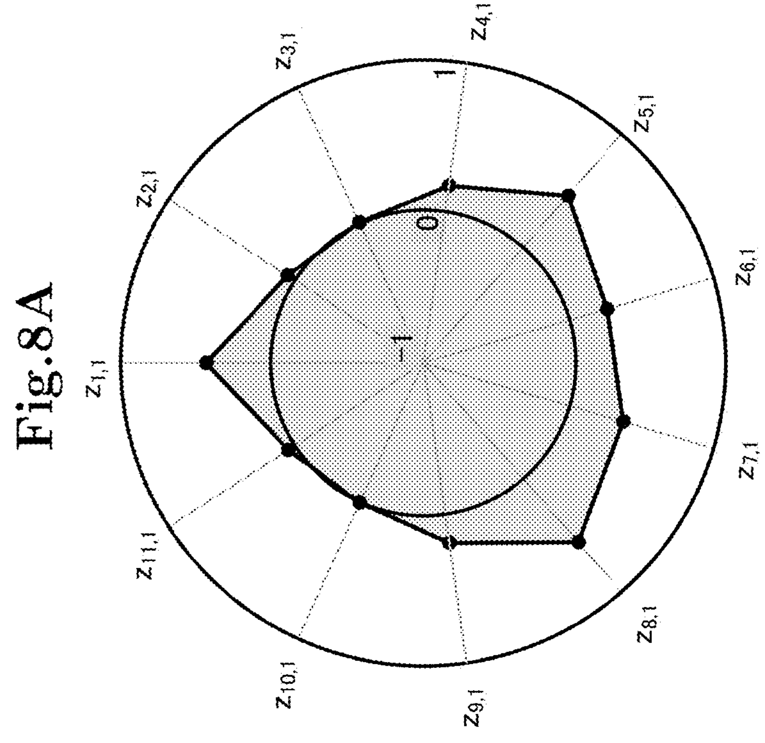
FIGS. 8A and 8B illustrate an example of the result of singular value decomposition of a first matrix calculated by the analysis system of the first embodiment.
Figure 8B:
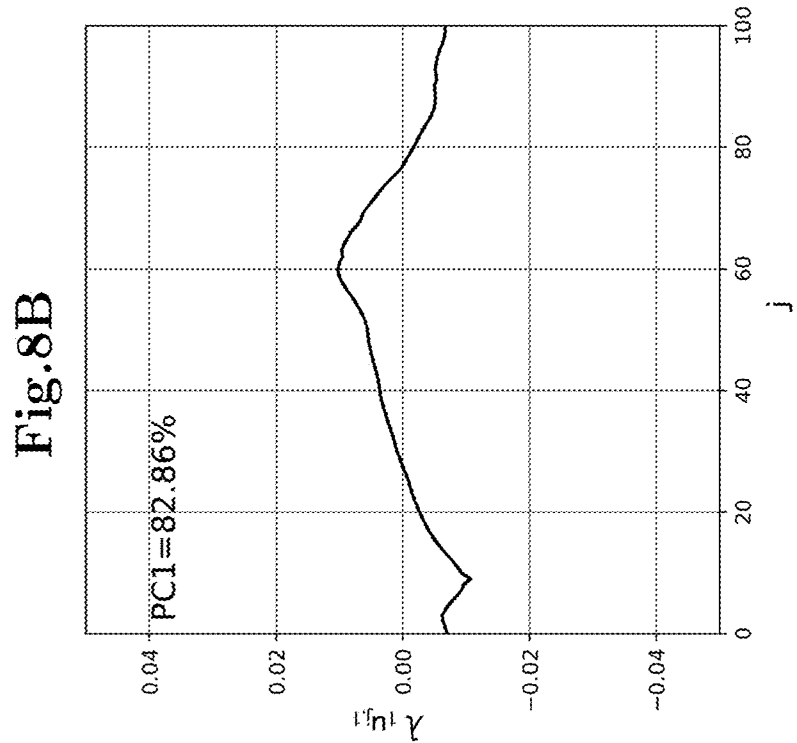

FIG. 8A illustrates an example of the right-singular vector (in this example, the first singular vector) $z_1$ corresponding to the singular value (in this example, the first singular value) $\lambda_1$ which is the largest among the singular values of the first matrix $A_1$. FIG. 8B illustrates an example of a vector $\lambda_{1u1}$ obtained by multiplying the singular value (in this example, the first singular value) $\lambda_1$ which is the largest among the singular values of the first matrix $A_1$ to the left-singular vector $u_1$ corresponding to the singular value $\lambda_1$.

Figure 9A:
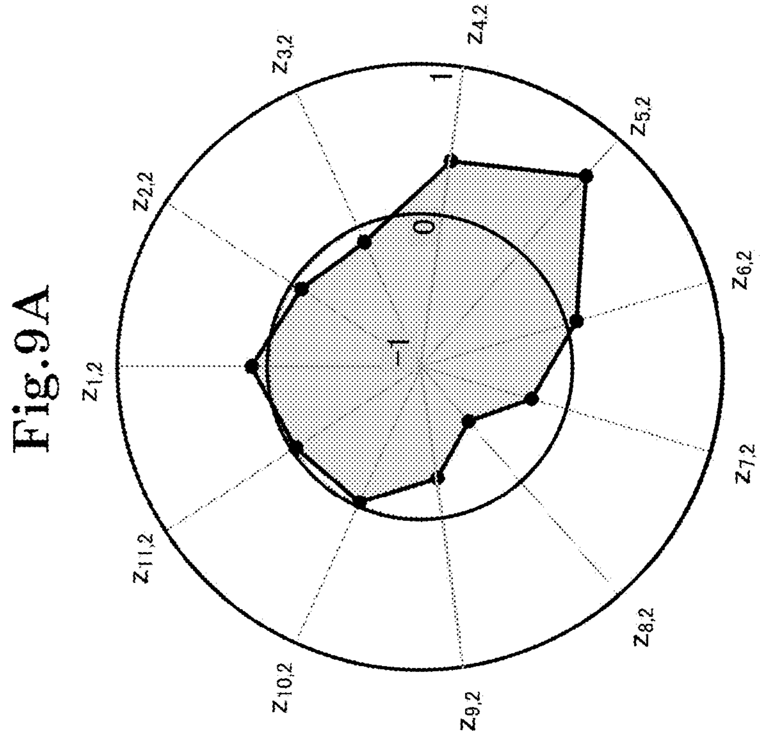
FIGS. 9A and 9B illustrate an example of the result of singular value decomposition of a first matrix calculated by the analysis system of the first embodiment.
Figure 9B:
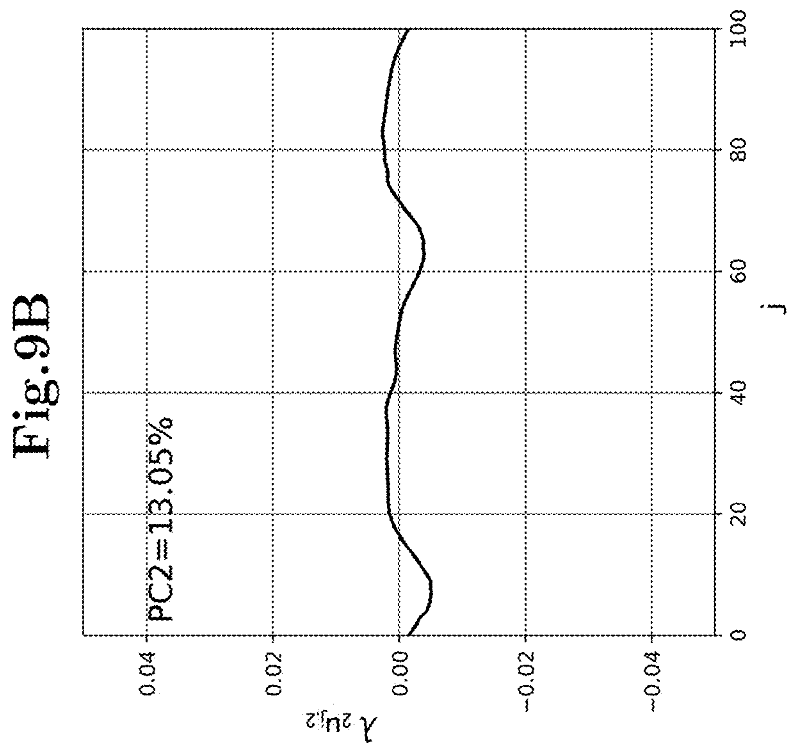

FIG. 9A illustrates an example of the right-singular vector $z_2$ corresponding to the singular value $\lambda_2$ which is the second largest among the singular values of the first matrix $A_1$. FIG. 9B illustrates an example of a vector $\lambda_{2u2}$ obtained by multiplying the singular value $\lambda_2$ which is the second largest among the singular values of the first matrix $A_1$ to the left-singular vector $u_2$ corresponding to the singular value $\lambda_2$.

FIGS. 10A, 10B, 11A and 11B are graphs illustrating an example of the results of singular value decomposition of the second matrix $A_2$ calculated by the analysis system 1 of the first embodiment.

Figure 10A:
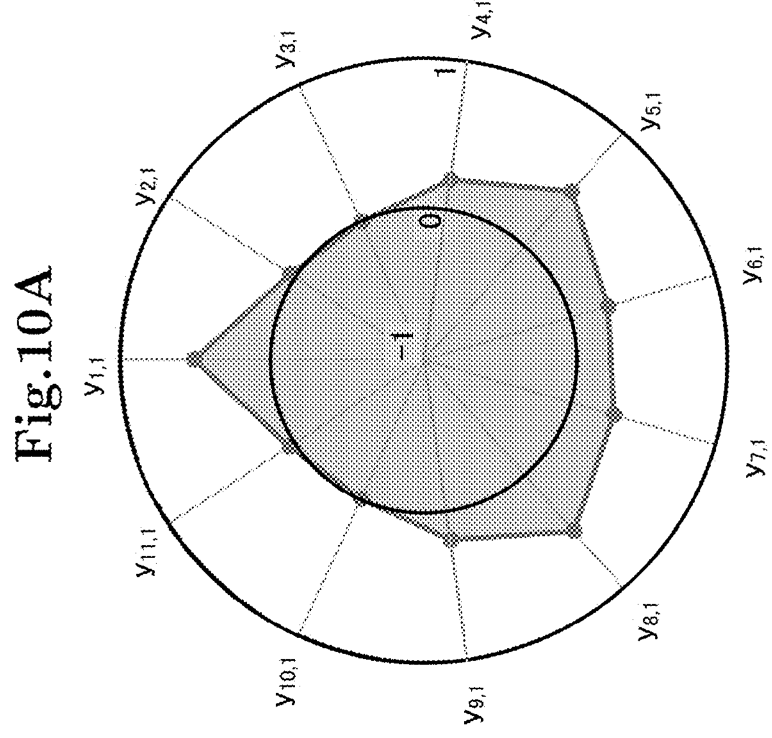
FIGS. 10A and 10B illustrate an example of the result of singular value decomposition of a second matrix calculated by the analysis system of the first embodiment.
Figure 10B:
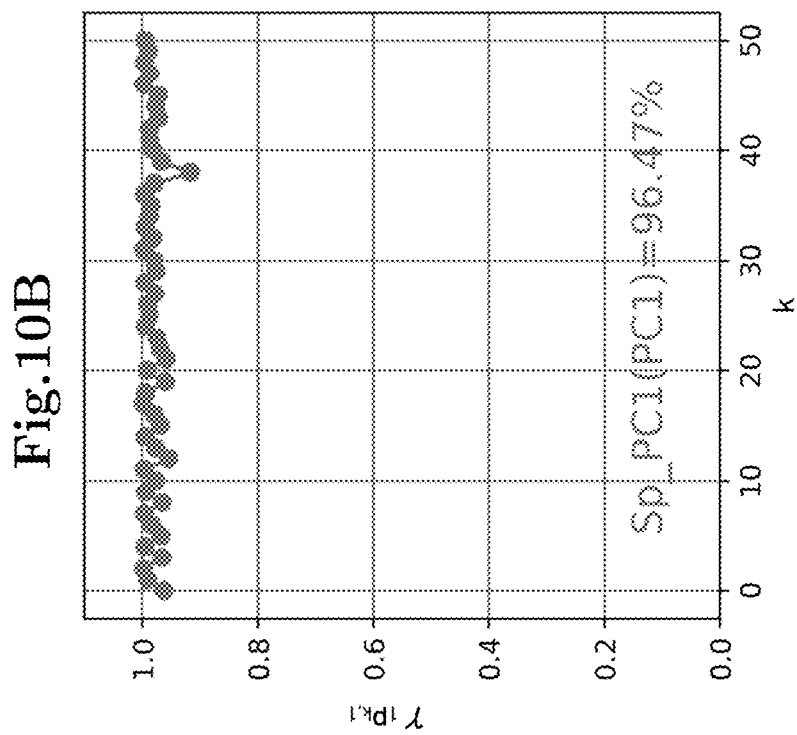

FIG. 10A illustrates an example of the right-singular vector $\gamma_1$ corresponding to the singular value $\gamma_1$ which is the largest among the singular values of the second matrix $A_2$. FIG. 10B illustrates an example of a vector $\gamma_1 p_1$ obtained by multiplying the singular value $\gamma_1$ which is the largest among the singular values of the second matrix $A_2$ to the left-singular vector $p_1$ corresponding to the singular value $\gamma_1$.

Figure 11A:
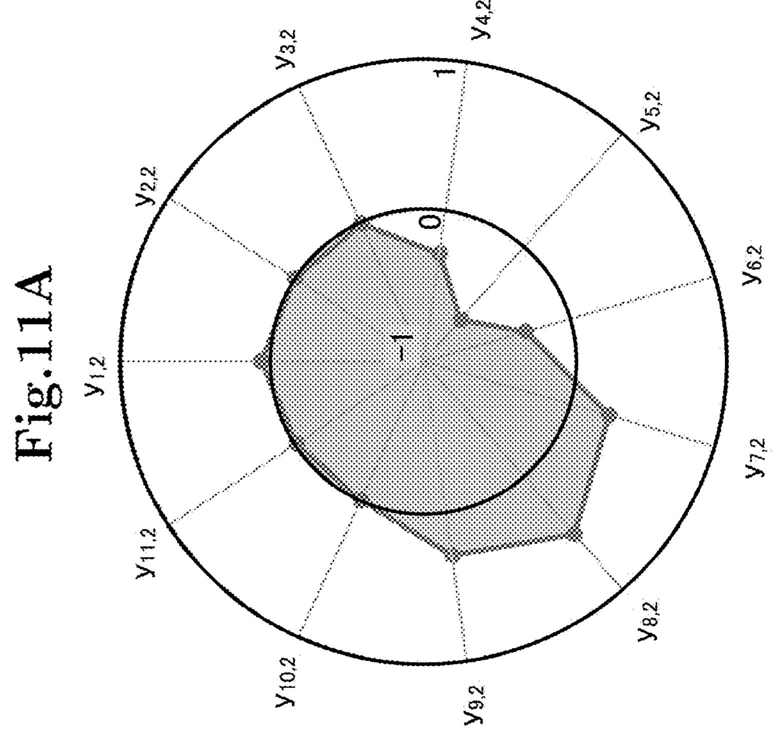
FIGS. 11A and 11B illustrate an example of the result of singular value decomposition of a second matrix calculated by the analysis system of the first embodiment.
Figure 11B:
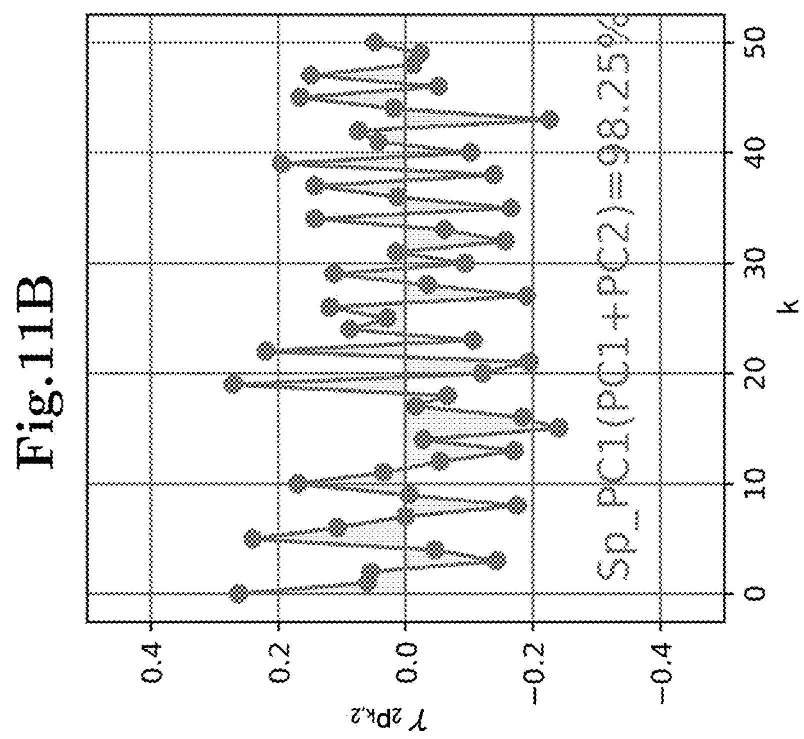

FIG. 11A illustrates an example of the right-singular vector $\gamma_2$ corresponding to the singular value (in this example, the second singular value) $\gamma_2$ which is the second largest among the singular values of the second matrix $A_2$. FIG. 11B illustrates an example of a vector $\gamma_2 p_2$ obtained by multiplying the singular value (in this example, the second singular value) $\gamma_2$ which is the second largest among the singular values of the second matrix $A_2$ to the left-singular vector (in this example, the second singular vector) $p_2$ corresponding to the singular value $\gamma_2$.

By the way, the generation device 10 of the first embodiment acquires the visible light video information and the distance video information by input from the imaging device 50. The generation device 10 of a modified example of the first embodiment may acquire the visible light video information and the distance video information by receiving these information from another device communicably connected to the generation device 10. Alternatively, the generation device 10 of a modified example of the first embodiment may acquire the visible light video information and the distance video information by reading these information from a recording medium.

By the way, the analysis device 20 of the first embodiment acquires the visible light video information and the distance video information by input from the imaging device 60. The analysis device 20 of a modified example of the first embodiment may acquire the visible light video information and the distance video information by receiving these information from another device communicably connected to the analysis device 20. Alternatively, the analysis device 20 of a modified example of the first embodiment may acquire the visible light video information and the distance video information by reading these information from a recording medium.

By the way, each of the generation device 10 and the analysis device 20 of the first embodiment acquires the angular momentum information based on both the visible light video information and the distance video information. Each of the generation device 10 and the analysis device of a modified example of the first embodiment may acquire the angular momentum information based on either the visible light video information or the distance video information.

Alternatively, each of the generation device 10 and the analysis device 20 of a modified example of the first embodiment may acquire the angular momentum information based on detection information instead of or in addition to the visible light video information and the distance video information. For example, the detection information may be information acquired by using a sensor or a marker attached to each of the constitution bodies.

By the way, the analysis device 20 of the first embodiment acquires the characteristic information for the target of interest based on the trained model generated by the generation device 10. The analysis device 20 of a modified example of the first embodiment may acquire the characteristic information for the target of interest without using the trained model. In this case, the analysis device 20 may acquire the element for the target of interest of the second singular vector as the characteristic information for the target of interest by acquiring the first singular vector for each of the learning targets and the target of interest, and acquiring the second singular vector based on the acquired first singular vectors. Alternatively, the analysis device 20 of a modified example of the first embodiment may, for the target of interest, acquire the first singular vector based on the angular momentum information, and use the acquired first singular vector as the characteristic information.

The present disclosure is not limited to the embodiment described above. For example, various modifications that can be understood by those skilled in the art may be made to the embodiment described above within the range without departing from the spirit of the present disclosure.

The invention claimed is:

1. An analysis device that analyzes a motion of a target with constitution bodies connected to each other, the analysis device comprising:

angular momentum information acquisition processor circuitry configured to acquire angular momentum information representing a time series of angular momentum for each of the constitution bodies; and characteristic information acquisition processor circuitry configured to acquire characteristic information, the characteristic information being based on a first singular vector and representing a characteristic of the motion, the first singular vector corresponding to a first singular value and having elements respectively corresponding to the constitution bodies, the first singular value being the largest among singular values of a first matrix whose elements are the angular momentum information for the constitution bodies, respectively, output processor circuitry configured to output information representing a degree of normality of the motion based upon the characteristic information, wherein the characteristic information is based on an element of a second singular vector, the element corresponding to a target of interest among targets, the second singular vector corresponding to a second singular value and having elements respectively corresponding to the targets, the second singular value being the second largest among singular values of a second matrix whose elements are the first singular vectors for the targets, respectively.

2. The analysis device according to claim 1, wherein the characteristic information acquisition processor circuitry configured to acquire the characteristic information based on a trained model and the angular momentum information for the target of interest, and the trained model is generated by:

acquiring a second singular vector, the second singular vector corresponding to a second singular value and having elements respectively corresponding to learning targets, the second singular value being the second largest among singular values of a second matrix whose elements are the first singular vectors for the respective-learning targets, respectively; and learning teaching data for each of the learning targets, the teaching data including the angular momentum information of the learning target and information based on an element of the second singular vector, the element corresponding to the learning target.

3. The analysis device according to claim 1, wherein the target is a human with paralysis in a half of the body on left side or right side, and the constitution bodies include:

a pelvic region;

a forearm, an upper arm, a thigh, a lower leg, and a foot, each included in the half of the body with paralysis; and a forearm, an upper arm, a thigh, a lower leg, and a foot, each included in another half of the body without paralysis.

4. The analysis device according to claim 1, wherein the motion is a gait, and the angular momentum information corresponds to a period with two steps composed of one step on each side.

5. The analysis device according to claim 1, wherein the characteristic information is acquired to reflect a characteristic which is unique to the motion of the target of interest in the targets.

6. An analysis method that analyzes a motion of a target with constitution bodies connected to each other, the analysis method including:

acquiring angular momentum information representing a time series of angular momentum for each of the constitution bodies; and acquiring characteristic information, the characteristic information being based on a first singular vector and representing a characteristic of the motion, the first singular vector corresponding to a first singular value and having elements respectively corresponding to the constitution bodies, the first singular value being the largest among singular values of a first matrix whose elements are the angular momentum information for the constitution bodies, respectively, outputting information representing a degree of normality of the motion based upon the characteristic information, wherein the characteristic information is based on an element of a second singular vector, the element corresponding to a target of interest among targets, the second singular vector corresponding to a second singular value and having elements respectively corresponding to the targets, the second singular value being the second largest among singular values of a second matrix whose elements are the first singular vectors for the targets, respectively.

7. The analysis method according to claim 6, wherein the characteristic information is acquired to reflect a characteristic which is unique to the motion of the target of interest in the targets.

8. The analysis method according to claim 6, wherein the acquiring of the characteristic information is based on a trained model and the angular momentum information for the target of interest, and the trained model is generated by:

acquiring a second singular vector, the second singular vector corresponding to a second singular value and having elements respectively corresponding to learning targets, the second singular value being the second largest among singular values of a second matrix whose elements are the first singular vectors for the learning targets, respectively; and learning teaching data for each of the learning targets, the teaching data including the angular momentum information of the learning target and information based on an element of the second singular vector, the element corresponding to the learning target.

9. The analysis method according to claim 6, wherein the target is a human with paralysis in a half of the body on left side or right side, and the constitution bodies include:

a pelvic region;

a forearm, an upper arm, a thigh, a lower leg, and a foot, each included in the half of the body with paralysis; and a forearm, an upper arm, a thigh, a lower leg, and a foot, each included in another half of the body without paralysis.

10. The analysis method according to claim 6, wherein the motion is a gait, and the angular momentum information corresponds to a period with two steps composed of one step on each side.

11. A generation device that generates a trained model used to analyze a motion of a target with constitution bodies connected to each other, the generation device comprising:

angular momentum information acquisition processor circuitry configured to acquire angular momentum information for each of learning targets, the angular momentum information representing a time series of angular momentum for each of the constitution bodies;

first singular vector acquisition processor circuitry configured to acquire a first singular vector for each of the learning targets, the first singular vector corresponding to a first singular value and having elements respectively corresponding to the constitution bodies, the first singular value being the largest among singular values of a first matrix whose elements are the angular momentum information for the constitution bodies, respectively;

second singular vector acquisition processor circuitry configured to acquire a second singular vector, the second singular vector corresponding to a second singular value and having elements respectively corresponding to the learning targets, the second singular value being the second largest among singular values of a second matrix whose elements are the first singular vectors for the learning targets, respectively;

a model generator configured to generate the trained model by learning teaching data for each of the learning targets, the teaching data including the angular momentum information of the learning target and information based on an element of the second singular vector, the element corresponding to the learning target, wherein the trained model is used to acquire characteristic information representing a characteristic of a motion of a target of interest; and output processor circuitry configured to output information representing a degree of normality of the motion based upon the characteristic information.

12. The generation device according to claim 11, wherein the target is a human with paralysis in a half of the body on left side or right side, and the constitution bodies include:

a pelvic region;

a forearm, an upper arm, a thigh, a lower leg, and a foot, each included in the half of the body with paralysis; and a forearm, an upper arm, a thigh, a lower leg, and a foot, each included in another half of the body without paralysis.

13. The generation device according to claim 11, wherein the motion is a gait, and the angular momentum information corresponds to a period with two steps composed of one step on each side.

14. The generation device according to claim 11, wherein the characteristic information is acquired to reflect a characteristic which is unique to the motion of the target of interest in the learning targets.

* * * * *